US00PP26826P2

(12) United States Plant Patent
Kolk

(10) Patent No.: US PP26,826 P2
(45) Date of Patent: Jun. 14, 2016

(54) ***HYDRANGEA* PLANT NAMED 'SPIKE'**

(50) Latin Name: *Hydrangea macrophylla*
Varietal Denomination: Spike

(71) Applicant: Bartholomeus Petrus Maria Kolk, Amstelveen (NL)

(72) Inventor: Bartholomeus Petrus Maria Kolk, Amstelveen (NL)

( * ) Notice: Subject to any disclaimer, the term of this patent is extended or adjusted under 35 U.S.C. 154(b) by 136 days.

(21) Appl. No.: 13/999,749

(22) Filed: Mar. 19, 2014

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

Concept Plants *Hydrangea macrophylla* Spike ('Kolk25' PPAF) 2014, retrieved on Sep. 17, 2015, retrieved from the Internet at <http://conceptplants.com/plant/?p=hymh213> 1 page.*
Rice. My Garden The RHS's online community for gardeners, Graham Rice's New Plants Blog. *Hydrangea beautensia* Spike: New ruffled *Hydrangea* from Crocus 2012, retrieved on Sep. 28, 2015, retrieved from the Internet at <http://mygarden.rhs.org.uk/blogs/graham_rice/archive/2012/03/04/hydrangea-beautensia-spike-new-ruffled-hydrangea-from-crocus.aspx> 2 pp.*

* cited by examiner

*Primary Examiner* — June Hwu
(74) *Attorney, Agent, or Firm* — Penny J. Aguirre

(57) ABSTRACT

A new cultivar of *Hydrangea macrophylla* named 'Spike' that is characterized by its single sterile flowers that are a blend of pink shades in color with crinkled and wavy sepals, its strong stems, and its free flowering habit with sturdy inflorescences.

2 Drawing Sheets

Genus/species: *Hydrangea macrophylla.*
Varietal denomination: 'Spike'.

BACKGROUND OF THE INVENTION

The present invention relates to a new and distinct cultivar of *Hydrangea macrophylla* and will be referred to hereafter by its cultivar name, 'Spike'. 'Spike' represents a new bigleaf *hydrangea*, a perennial shrub grown for landscape use.

The Inventor discovered the new cultivar in 2006 as a naturally occurring branch mutation of *Hydrangea* 'Challenge' (not patented) that was growing in a container in Amstelveen, The Netherlands.

Asexual propagation of the new cultivar was first accomplished by softwood stem cuttings by the Inventor in Amstelveen, The Netherlands in 2006. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Spike' as a unique cultivar of *Hydrangea macrophylla.*

1. 'Spike' exhibits single sterile flowers that are a blend of pink shades in color.
2. 'Spike' exhibits sterile flowers with crinkled and wavy sepals.
3. 'Spike' exhibits strong stems.
4. 'Spike' is free flowering with sturdy inflorescences.

The parent plant of 'Spike', 'Challenge', differs from 'Spike' in having sterile flowers that lack crinkled sepals. 'Spike' can be most closely compared to the cultivar 'Blue Heaven' (U.S. Plant Pat. No. 18,823). 'Blue Heaven' is similar to 'Spike' in plant size, inflorescence size and in having strong stems. 'Blue Heaven' differs from 'Blue Heaven' in having sterile flowers that lack crinkled sepals. There are no cultivars of *Hydrangea macrophylla* known to the Inventor that have sterile flowers with sepals that are crinkled in the manner of 'Spike'.

BRIEF DESCRIPTION OF THE DRAWINGS

The photographs in the figures were taken of a two year-old plant of 'Spike' as grown in an unheated greenhouse in alkaline soil in a 15-liter container in Amstelveen, The Netherlands.

The photograph in FIG. 1 illustrates a side view of 'Spike' in bloom.

Figure 1:
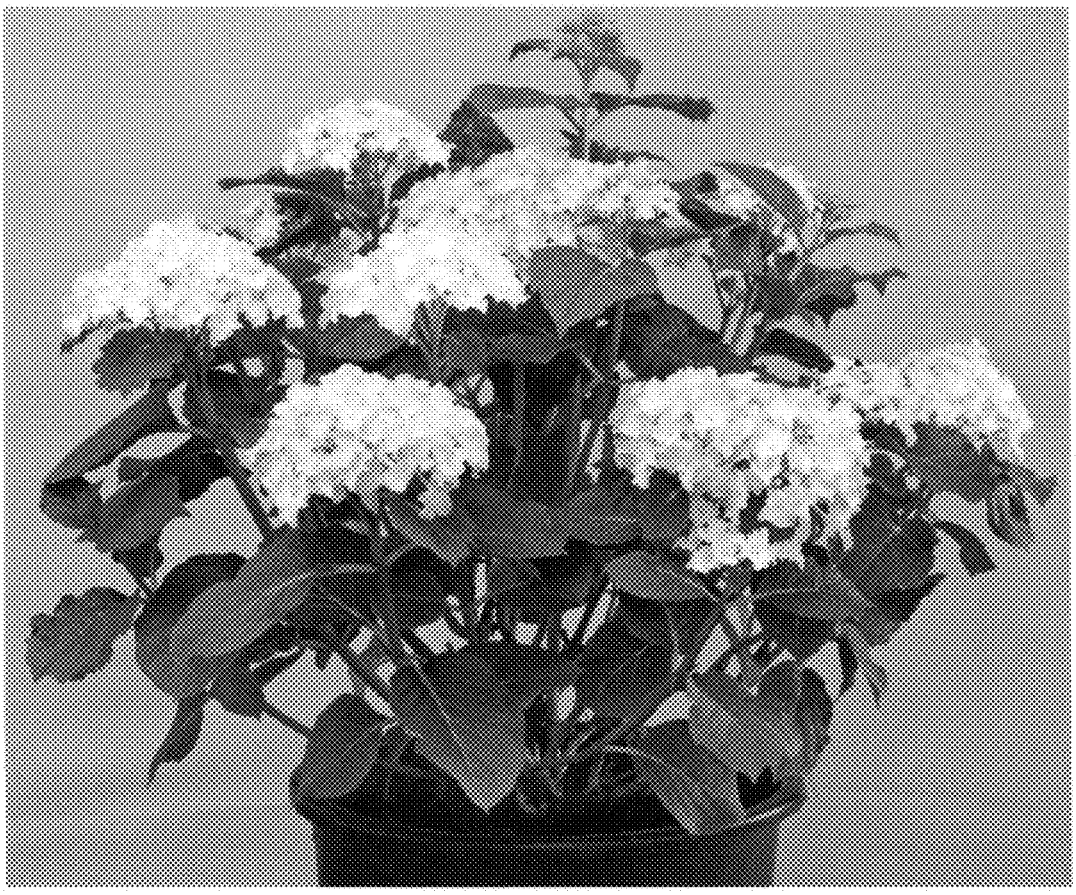
Figure 2:
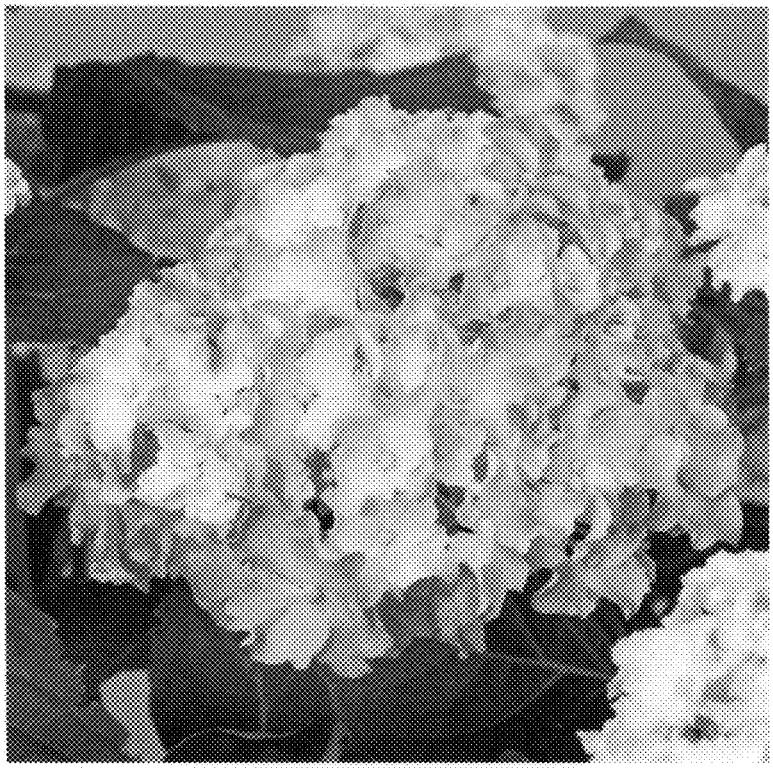

The photograph in FIG. 2 provides a close-up view of an inflorescence of 'Spike'.

Figure 3:
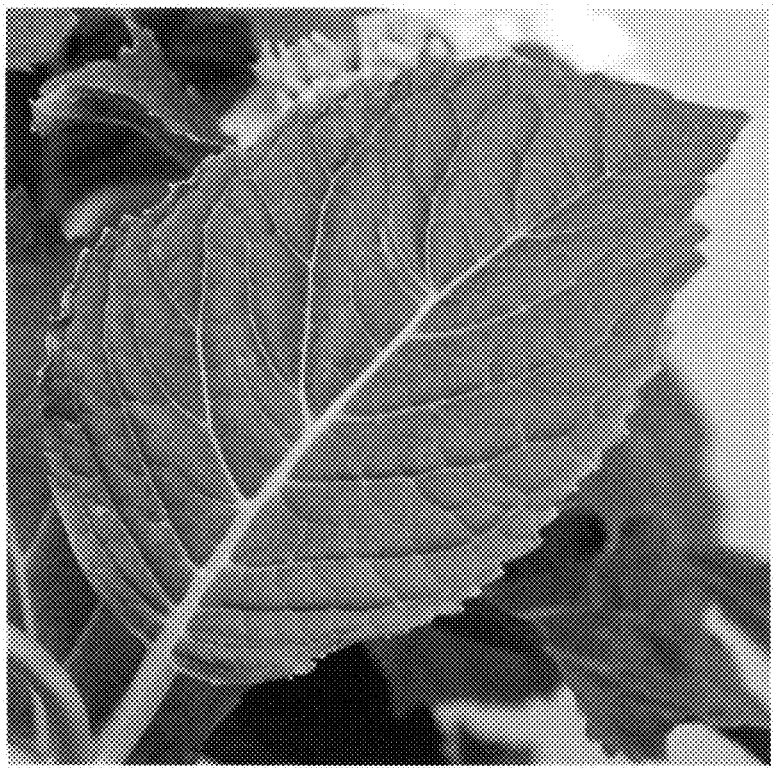

The photograph in FIG. 3 provides a close-up view of a leaf of 'Spike'.

The colors in the photographs are as close as possible with the digital photography and printing techniques utilized and the color codes in the detailed botanical description accurately describe the new *Hydrangea.*

BOTANICAL DESCRIPTION OF THE PLANT

The following is a detailed description of two year-old plants as grown under greenhouse conditions in alkaline soil in 15-liter containers in an unheated greenhouse in Amstelveen, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late spring to late summer in The Netherlands.

*Plant type.*—Deciduous shrub.

*Plant habit.*—Broadly upright, sturdy, overall globular in shape.

*Height and spread.*—Average 62 cm in height and 80 cm in diameter.

*Hardiness.*—At least in U.S.D.A. Zones 5 to 9.

*Diseases resistance.*—Not more susceptible or resistant to pests and diseases than other *Hydrangea macrophylla* cultivars.

*Root description.*—Fibrous, dense, moderately branched.

*Propagation.*—Softwood stem cuttings.

*Growth rate and vigor.*—Moderate.

Stem description:

*Stem shape.*—Round.

*Stem strength.*—Strong.

*Stem aspect.*—Upright to an average angle of 70°.

*Stem color.*—Immature stem; 144A to 144B, mature stem; ranging between 199B to 199C.

*Stem size.*—Average of 26.5 cm in length (including peduncle) and 8 mm in diameter.

*Stem surface.*—Smooth and sparsely covered with lenticels and average of 2 per cm, 3 mm in length and 1 mm in width and 200A in color.

*Branching.*—Moderately freely branching, with an average of 26 lateral branches.

*Internode length.*—Average of 5.6 cm.

Foliage description:

*Leaf shape.*—Broad ovate to broad obovate.

*Leaf arrangement.*—Opposite.

*Leaf division.*—Simple.

*Leaf number.*—Average of 8 (4 pairs) per lateral branch.

*Leaf base.*—Short attenuate.

*Leaf apex.*—Short apiculate.

*Leaf margins.*—Serrated.

*Leaf venation.*—Pinnate, upper surface; 144C, lower surface; 144C to 144D.

*Leaf size.*—Average of 12.1 cm in length and 9.3 cm in width.

*Leaf attachment.*—Petiolate.

*Leaf surface.*—Upper and lower surface; smooth and slightly rugose.

*Leaf color.*—Immature upper surface; a color between 141A and 143B, immature lower surface; 138A, mature upper surface; N137A to N137B, mature lower surface; 147B.

*Petioles.*—Average of 2.1 cm in length and 4 mm in width, upper and lower surfaces; 144C in color and surfaces are smooth to moderately glossy.

Inflorescence description:

*Inflorescence type.*—Flattened globular, mophead form, compound corymb of single sterile and fertile flowers.

*Lastingness of inflorescence.*—Sterile flowers; persistent, lasting about 6 weeks, fertile flowers; self-cleaning, lasting about 1 week.

*Inflorescence number.*—One per lateral or sublateral stem.

*Inflorescence size.*—Average of 11.5 cm in height and 16.8 cm in diameter.

*Flower number.*—An average of 100 sterile flowers and 75 fertile flowers per inflorescence.

*Flower fragrance.*—None.

*Flower aspect.*—Sterile flowers; upright and slightly outward, fertile flowers; upright.

*Flower size.*—Sterile flowers; rotate, average of 4.1 cm in diameter and 1.1 cm in depth, fertile flowers; rotate, average of 9 mm in diameter and 7 mm in depth.

*Flower buds.*—Sterile flowers; average of 6 mm in length and 5 mm in diameter, obovate in shape and 145A in color, fertile flowers; average of 7 mm in length and 5 mm in diameter, broad ovate in shape and 65D in color.

*Peduncles.*—Average of 6 cm in length and 4 mm in width, strong, 144A to 144B in color, surface is smooth and sparsely covered with lenticels and average of 2 per cm, 3 mm in length and 1 mm in width and 200A in color.

*Pedicels.*—Sterile Flowers; average of 2.3 cm in length and 1.8 mm in diameter, held at an average angle of 30°, strong, 65B in color, surface is covered with dull pubescent thin hairs, average of 0.5 mm in length and to small to be measured by RHS-CC, fertile flowers; average of 6 mm in length and 1 mm in diameter, at an average angle of 10°, moderate in strength, 65B in color, surface is sparsely covered with dull pubescent short thin hairs, average of 0.5 mm in length and to small to be measured by RHS-CC.

*Petals.*—Sterile flowers; average of 4 in a cross-like arrangement, broad elliptic to concave in shape, acute apex, cuneate base, entire margin, average of 4 mm in length and 3 mm in width, upper and lower surface texture is smooth and dull, color: upper surface when opening; 65B, base 65D, lower surface when opening; 62D, upper surface when fully opened; 65B, base 65D, lower surface when fully opened; 62D, fertile flowers; average of 5 in a rotate arrangement, elliptic to ovate, concave in shape, acute apex, cuneate base, entire margin, average of 5 mm in length and 3 mm in width, upper and lower surface texture is smooth and dull, color: upper surface when opening; a blend of 155A, 145C, and 68D, lower surface when opening; a blend of 155A, 145C, and 69C to 69D, upper surface when fully opened; 68C, lower surface when fully opened; 69C and flushed with 145D.

*Sepals.*—Sterile flowers; average of 4, rotate (cross-like) in arrangement, medium to strongly overlapping, both surfaces smooth and dull, ovate to broad elliptic in shape, margin is strongly wavy to crinkled and curled, bluntly acute apex, cuneate base, an average of 2.3 cm in length and 2.4 cm in width, color: upper surface when opening; 69B to 69C becoming 62B at the tip, lower surface when opening; N155B, flushed with 69C to 69D, upper surface when fully open; 63C, lower surface when fully open; 62B to 62C, fading to upper side; 63B, fading to lower side; 62A to 62B, fertile flowers; average of 4, rotate in arrangement, both surfaces smooth and dull, broad ovate in shape, margin is entire, acute apex, broad cuneate base, an average of 2 mm in length and 2 mm in width, color: upper and lower surface when opening; 144A, base is 145B, upper and lower surface when fully open; 144A, base is 145B.

Reproductive organs:

*Androecium.*—Sterile flowers; average of 8 stamens, filaments are 3 mm in length and 62A in color, anther is broad kidney-shaped, 1.2 mm in length and 156D in color, pollen is low in quantity and 158D in color, fertile flowers; average of 8 stamens, filaments are 3 mm in length and 68C in color, anthers are broad kidney-shaped, 1.5 mm in length and 157A in color, pollen is moderate in quantity and 158D in color.

*Gynoecium.*—Sterile flowers; average of 3 pistils, 2.5 mm in length, stigma is club-shaped and 62D in color, style is 1.8 mm in length and 156D in color, ovary is 62B to 62C in color, fertile flowers; average of 3 pistils 2 mm in length, stigma is club-shaped and 157D in color, style is 0.5 mm in length and 157D in color and ovary is 145D in color.

*Fruit and seed.*—No seeds or fruit observed to date.

It is claimed:

1. A new and distinct cultivar of *Hydrangea* plant named 'Spike' substantially as herein illustrated and described.

* * * * *